(12) United States Patent
Davis et al.

(10) Patent No.: US 6,780,839 B2
(45) Date of Patent: Aug. 24, 2004

(54) USE OF SECRETIN-RECEPTOR LIGANDS IN TREATMENT OF CYSTIC FIBROSIS (CF) AND CHRONIC OBSTRUCTIVE PULMONARY DISEASE (COPD)

(75) Inventors: Richard J. Davis, Hertfordshire (GB); Keith J. Page, Hertfordshire (GB)

(73) Assignee: Pharmagene Laboratories Ltd., Hertfordshire (GB)

( * ) Notice: Subject to any disclaimer, the term of this patent is extended or adjusted under 35 U.S.C. 154(b) by 36 days.

(21) Appl. No.: 09/897,412

(22) Filed: Jul. 3, 2001

(65) Prior Publication Data

US 2002/0142956 A1 Oct. 3, 2002

(30) Foreign Application Priority Data

Jul. 4, 2000 (GB) .............................. 0016441

(51) Int. Cl.[7] .................. A61K 38/00; A61K 38/04
(52) U.S. Cl. ................ 514/2; 514/12; 530/300; 530/324
(58) Field of Search ............... 514/2, 12, 4, 8, 514/21, 851; 530/300, 324, 350

(56) References Cited

U.S. PATENT DOCUMENTS

| | | | |
|---|---|---|---|
| 3,833,722 A | 9/1974 | Graybill | |
| 5,428,015 A | 6/1995 | Kurono et al. | |
| 6,020,310 A | * 2/2000 | Beck et al. | 514/12 |
| 6,020,314 A | 2/2000 | McMichael | |
| 6,498,143 B1 | * 12/2002 | Beck et al. | 514/12 |
| 2002/0099023 A1 | * 7/2002 | Boucher | 514/23 |

FOREIGN PATENT DOCUMENTS

| | | |
|---|---|---|
| WO | WO 95/06724 | 3/1995 |
| WO | WO 95/27496 | 10/1995 |
| WO | WO 97/33616 | 9/1997 |
| WO | WO 98/02453 | 1/1998 |
| WO | WO 98/52593 | 11/1998 |
| WO | WO 99/64059 | 12/1999 |

OTHER PUBLICATIONS

Kanno et al. (Sep. 2001) "Regulation of cholangiocyte bicarbonate secretion." Am. J. Physiol Gastrointest. Live. Physiol. 281(3): G612–G625.*

Tietz et al. (May 30, 2003) "Agonist–induced Coordinated Trafficking of Functionally Related Transport Proteins for Water and Ions in Cholangiocytes." The Journal of Biological Chemistry 278(22): 20413–20419.*

Windstetter et al. (Oct. 30, 1997) "Renal Function and Renotropic Effects of Secretin in Cystic Fibrosis." Eur. J. Med. Res. 2(10): 431–436.*

Marinelli et al, Secretin Promotes Osmotic Water Transport in Rat Cholangiocytes . . . , The Journal of Bilogical Chemistry, vol. 272, No. 20, Issue of May 16, 1197, pp. 12984–12988.

(List continued on next page.)

Primary Examiner—Gary Kunz
Assistant Examiner—Christopher James Nichols
(74) Attorney, Agent, or Firm—Nixon & Vanderhye P.C.

(57) ABSTRACT

The invention is based on the finding that the secretin receptor is expressed in tissues present in the distal lung of humans. In patient with CF, levels of the receptor are elevated compared to normal tissue. Treatment of tissue by secretin stimulates the movement of negative ions in the tissue. The invention provides methods of treatment of cystic fibrosis or COPD in a patient by administering to said patient an effective amount of an agent which triggers anion efflux in respiratory tissue via the activation of a secretin receptor.

3 Claims, 9 Drawing Sheets

```
                         Mammalian Secretins 1              5               10                15
Human:    His-Ser-Asp-Gly-Thr-Phe-Thr-Ser-Glu-Leu-Ser-Arg-Leu-Arg-Glu-
Porcine:  His-Ser-Asp-Gly-Thr-Phe-Thr-Ser-Glu-Leu-Ser-Arg-Leu-Arg-Asp-
Canine:   His-Ser-Asp-Gly-Thr-Phe-Thr-Ser-Glu-Leu-Ser-Arg-Leu-Arg-Glu- 20             25
Human:    Gly-Ala-Arg-Leu-Gln-Arg-Leu-Leu-Gln-Gly-Leu-Val-NH$_2$    (SEQ ID NO:10)
Porcine:  Ser-Ala-Arg-Leu-Gln-Arg-Leu-Leu-Gln-Gly-Leu-Val-NH$_2$    (SEQ ID NO:11)
Canine:   Ser-Ala-Arg-Leu-Gln-Arg-Leu-Leu-Gln-Gly-Leu-Val-NH$_2$    (SEQ ID NO:12)
```

OTHER PUBLICATIONS

Gespach et al, Peptides, vol. 7, Suppl. 1, 155–163 (1986) "Secretin Receptor Activity in Rat Gastric Glands, Binding Studies, cAMP Generation and Pharmacology".

Mutt et al, Eur. J. Biochem. 15, (1970) 513–519 "Structure of Porcine Secretin".

Mutoh et al, Proc. Natl. Acad. Sci. vol. 94, 3560–3564 (1997) Biochemistry "The basic helix–loop–helix transcription factor BETA2/NeuroD is expressed in mamalian enteroendocrine cells and activates secretin gene expression".

Mutoh et al, Genes & Development 12:820–830 (1998) "The basic helix–loop protein BETA2 interacts with p300 to coordinate differentiation of secretin–expressing enteroendocrine cells".

Chang et al. The J. of Biological Chemistry, vol. 274, No. 16, 10758–10764 (1999) "Porcine Pancreatic Phospholipase $A_2$ Stimulates Secretin Release from Secretin–producing Cells".

Chang et al, Am. J. Physiol. 275 (Gastrointest. Liver Physiol. 38) G192–G202 (1998) "Modulation of secretin release by neuropeptides in secretin–producing cells".

Sexton, Current Opinion in Drug Discovery and Development, vol. 2(5), 440–488 (1999) "Recent advances in our understanding of peptide hormone receptors and RAMPS".

Stern et al, J. Royal College of Physicians of London, vol. 33, No. 5, 434–439 (1999) "The pathogenesis of cystic fibrosis and progress towards gene therapy".

Cross et al et al, Life Sciences, vol. 29, 895–922 (1981) Synthesis, Biological and Immunochemical Properties o Analogues of Secretin and Vasoactive Intestinal Peptide (VIP): The Vasectrins.

Fortner et al, Am. J. Physiol. Lung Cell Mol Physiol 280:L334–341 (2001) "Chloride channel function is linked to epithelium–dependent airway relaxation".

Wolf et al Chest, 89, 3, 327–330 (1986) "Demonstration of calcitonin and calmodulin by immunoperoxidase in the cystic fibrosis lung".

Chang et al, AJP–Gastrointestinal and Liver Physiology Abstract vol. 279, Issue 2, G295–G303 (2000) "Cellular mechanism of sodium oleate–stimulated secretion of cholecystokinin and secretin".

Xue et al, Medline Abstract, Dig Dis Sci 38:344–352 (1993) "Characterization of secretin release in secretin cell–enriched preparation isolated from canine duodenal mucosa".

* cited by examiner

FIGURE 1

Mammalian Secretins

```
          1               5                  10                  15
Human:    His-Ser-Asp-Gly-Thr-Phe-Thr-Ser-Glu-Leu-Ser-Arg-Leu-Arg-Glu-
Porcine:  His-Ser-Asp-Gly-Thr-Phe-Thr-Ser-Glu-Leu-Ser-Arg-Leu-Arg-Asp-
Canine:   His-Ser-Asp-Gly-Thr-Phe-Thr-Ser-Glu-Leu-Ser-Arg-Leu-Arg-Glu- 20                  25
Human:    Gly-Ala-Arg-Leu-Gln-Arg-Leu-Leu-Gln-Gly-Leu-Val-NH₂  (SEQ ID NO:10)
Porcine:  Ser-Ala-Arg-Leu-Gln-Arg-Leu-Leu-Gln-Gly-Leu-Val-NH₂  (SEQ ID NO:11)
Canine:   Ser-Ala-Arg-Leu-Gln-Arg-Leu-Leu-Gln-Gly-Leu-Val-NH₂  (SEQ ID NO:12)
```

USE OF SECRETIN-RECEPTOR LIGANDS IN TREATMENT OF CYSTIC FIBROSIS (CF) AND CHRONIC OBSTRUCTIVE PULMONARY DISEASE (COPD)

FIELD OF THE INVENTION

The present invention relates to the treatment of cystic fibrosis (CF) and chronic obstructive pulmonary disease (COPD) with or by activation of the hormone secretin or other secretin receptor ligands.

BACKGROUND TO THE INVENTION

Cystic Fibrosis.

Cystic fibrosis (CF) is the most common, fatal, autosomal recessive inherited disease, with over 7000 people currently diagnosed in the UK alone and approximately 30,000 in the United States. The incidence of CF is strongly dependent on ethnic background. Caucasian individuals with Northern European ancestry are most at risk exhibiting a probability of approximately 1 in 2500, based on a heterozygous carrier rate of about 1 in 25.

CF arises as a result of genetic mutation(s) in the gene of the cystic fibrosis transmembrane regulator (CFTR) chloride channel throughout the body. Such mutations in the CFTR lead either to incorrect folding of the protein and/or the lack of migration of the transcribed protein from the Endoplasmic Reticulum to the epithelial plasma membrane and subsequent loss of chloride (Cl—) channel function. This causes a cellular and luminal imbalance in fluid and electrolyte transport and volume within the lower respiratory tract of the CF lung, which reduces the constitution of the mucus which in turn impairs mucociliary clearance and initiates the inevitable and persistent bacterial infections within the lung of CF patients. Different mutations give rise to CF symptoms of varying severity and correspondingly lead to variations in patient survival rates.

Over the last few decades, improved drug and physiotherapy treatments have improved patient survival time significantly, though average life expectancy is still short, currently around 30 years. There is therefore a continuing need to develop better treatment for this condition.

COPD

Clinical features of COPD include breathlessness, cough and sputum, with chronic airway obstruction and lung hyperinflation as a result of chronic bronchitis and emphysema (dilation of the distal lung airspaces). Chronic bronchial hyperactivity which is prominent in bronchial asthma is also found in COPD. Airway remodelling in COPD leads to persistent and irreversible airway narrowing and mucus hypersecretion. The direct cause of airway narrowing and hyperresponsiveness is unknown although it is generally proposed that abnormalities in the airway smooth muscle function results in decreased or impaired relaxation or increased contractility.

A bronchodilator regimen combining a slow release oral theophylline with an inhaled beta 2 agonist (e.g. ipratropium, salbutamol, salmeterol), and high dose inhaled steroids represent current therapies utilised in the treatment of COPD, because even modest improvement in obstruction is beneficial in COPD patients. Beta 2 agonist mediate bronchodilation of the airways via the stimulation of specific receptors which are coupled to the specific G-protein $G_s$, which in turn leads to an increase in the intracellular levels of the second messenger cAMP.

Recently Cl$^-$ ion movement has been demonstrated to be linked to epithelium-dependent airway relaxation (Fortner et al, 2001), such that blockade of Cl$^-$ ion secretion results in a significant reduction in agonist-induced relaxation. Additionally, compounds such as furosemide, a Cl$^-$ dependent Na$^+$/K$^+$/2Cl$^-$ co-transport inhibitor has been demonstrated, in some studies to decrease bronchial hyperresponsiveness in asthmatics (Pendino et al, 1998)). In addition, mucus hypersecretion and non-continuous clearance of tracheobronchial mucus also contribute to persistent airflow obstruction plugs, which can be present simultaneously with airway responsiveness. Mucus plugging can result in small airway (e.g. tertiary bronchus) obstruction producing reduced maximal respiratory flow and slow forced lung emptying.

Secretin

Secretin is a peptide hormone which is secreted from S cells in the proximal small intestine (especially the duodenum and jejunum) in response to acidic contents leaving the stomach. The structure of porcine secretin has been known for some time and it has been isolated from porcine intestine and has been found to be constituted by a peptide composed of 27 amino acid residues (Mutt et al, 1970). Moreover, it has been found that bovine and porcine secretins are identical, and are also similar to canine secretin.

Although bovine and porcine secreting behave identically with human secretin in some respects they are not structurally identical. These animal secretins differ from the human secretin at positions 15 and 16. An alignment of human, porcine and canine secretin is shown in FIG. 1.

Secretin's physiological role is to stimulate water ($H_2O$) and bicarbonate ($HCO_3^-$) secretion from the pancreas, leading to the neutralisation of acidic chyme. Its actions are mediated via a seven transmembrane domain, G protein coupled receptor (GPCR), a member of the glucagon-secretin-vasoactive intestinal peptide structurally related superfamily of GPCRs (IUPHAR Receptor Compendium, 1998), for which the peptide exhibits nanomolar affinity. Secretin receptor stimulation mediates increases in intracellular cAMP, and the activation of protein kinase A (PKA).

Secretin is currently approved by the FDA to diagnose gastrinoma and assess pancreatic function. Anecdotal reports from "off-label" use of secretin in paediatric autism suggest that it may improve both physiological and behavioural symptoms associated with autism, a disorder characterized by severely impaired communication, social skills and development (see for example WO98/52593, U.S. Pat. No. 6,020,310 or U.S. Pat. No. 6,020,314). In Mar. 2000 Repligen Corporation (USA) announced it had initiated a Phase II clinical trial with secretin in children with autism, with the Phase II trial sites including the Mayo Clinic, the University of Rochester Medical Center and the Southwest Autism Research Center in collaboration with Phoenix Children's Hospital. Initial results of these trials suggest that secretin infusion may be beneficial in discrete groups of severely autistic children.

Secretin has also been proposed for the prophylaxis of the aspiration pneumonia syndrome (e.g. in EP0150760; AU3806485).

There are a wide number of reported synthetic and/or naturally occurring secretin peptide analogues and fragments (referred to herein as "secretin receptor ligands") which exhibit a wide range of potencies, efficacies and selectivity for the secretin receptor. These include, but are not limited to mono/poly substituted secretin analogues, secretin fragments, substituted secretin fragments, reduced peptide bond analogues (Gardner et al, 1976; Gardner et al, 1979; Waelbroeck et al, 1981; Konig et al, 1984; Staun-Olsen et al, 1986; Robbertecht et al, 1988; Haffer et al, 1991), and naturally occurring and synthetic analogues, fragment and chimeric peptides of the VIP/secretin family (including VIP (vasoactive intestinal peptide), gastric inhibitory peptide (GIP), PACAP (pituitary adenylate cyclase-activating polypetide), adrenomedullin, calcitonin, CGRP (alpha, beta and skin calcitonin gene related peptides), glucagon, glucagon-like peptide (GLP), growth hormone-releasing factor, parathyroid hormone (PTH) and its related protein (PTHrP), corticotrophin-releasing hormone (CRH) and amylin Many of these peptides (including glucagon, GLP, PACAP and VIP share significant amino acid homology, particularly in the amino terminus with secretin. All these peptides are though to adopt similar secondary structural characteristics, including one or two regions of amphipathic α-helical secondary structure, and appear to interact with their receptors in a well conserved manner (Sexton, 1999).

Also known are secretin-related receptor peptides, and associated analogues and fragments which exhibit affinity for the secretin receptor.

DISCLOSURE OF THE INVENTION

We have studied the expression levels of secretin receptor in tissue from patients with CF and COPD. We have found that in both normal individuals and patients with these disease conditions, secretin receptor is expressed in the distal regions of the lung, particularly the tertiary bronchus and parenchyma, with little or no measurable mRNA expression in more proximal regions of the lung. The expression of secretin receptor in these tissues has not previously been reported.

We have moreover surprisingly found that levels of secretin receptor mRNA in tertiary bronchus of CF patients are significantly elevated. This elevation is specific to CF, and not shared by patients with other lung disorders. The elevation was specific to tissue of the tertiary bronchus.

While not wishing to be bound by any one particular theory, we believe the action of secretin on ion movements in cells (see below) will counteract the effect of the CTFR deficiency associated with CF. Further, although the operation of the present invention does not rely upon any one particular theory, an explanation of the elevated levels of secretin receptor mRNA in tertiary bronchial tissue is that this is in response to the ion imbalance experienced in these cells.

Moreover, in patients with COPD there is increasing recognition that the role of ion efflux in the lungs of patients may be a critical target for therapeutic intervention. The secretin receptor is coupled to the G-protein, $G_s$, and therefore it can be envisaged that activation of the functional secretin receptor that has been identified herein on epithelial cells lining the distal human bronchus will result in the accumulation of intracellular cAMP, and subsequent bronchodilation (see also Ng et al, 1999). Moreover in other mucus hypersecretory lung diseases, such as cystic fibrosis and COPD, reduction of predominantly $Cl^-$ efflux alters the aqueous and ionic composition and subsequent viscosity of mucus and mucus secretions, leading to thick insipid mucus which impairs mucociliary clearance from the lung. Thus the stimulation of ion movement in such patients may thus be beneficial in the treatment of their disease.

Accordingly, the present invention provides a method of treatment of cystic fibrosis in a patient suffering from CF, the method comprising administering to said patient an effective amount of an agent which triggers anion efflux in respiratory tissue via the activation of a secretin receptor.

The invention further provides a method of treatment of COPD in a patient suffering from COPD, the method comprising administering to said patient an effective amount of an agent which triggers anion efflux in respiratory tissue via the activation of a secretin receptor.

The present invention is in one part based on the surprising finding by the inventors of elevated levels of secretin receptor mRNA in the tertiary bronchus of CF patients, and relates to the novel use of secretin in the treatment of cystic fibrosis. A preferred aspect of the invention is directed to the treatment of CF by the administration to the patient of a secretin receptor ligand. However, it has been contemplated by the inventors that secretin may be delivered to the patient in an effective amount by means other than directly administering the secretin receptor ligand itself. An alternative method of administering secretin is by the use of agents which stimulate the up-regulation of the production and or release of endogenous secretin in pulmonary cells, or secretin related peptides.

The invention also provides the use of an agent which triggers anion efflux in respiratory tissue via the activation of a secretin receptor for the manufacture of a medicament for the treatment of cystic fibrosis.

The invention additionally provides the use of an agent which triggers anion efflux in respiratory tissue via the activation of a secretin receptor for the manufacture of a medicament for the treatment of COPD.

Preferably, the agent is a secretin receptor ligand, more particularly secretin, particularly human secretin.

BRIEF DESCRIPTION OF THE DRAWINGS

FIG. 1 shows an alignment of human, porcine and canine secretin.

DETAILED DESCRIPTION OF THE INVENTION

Figure 2:
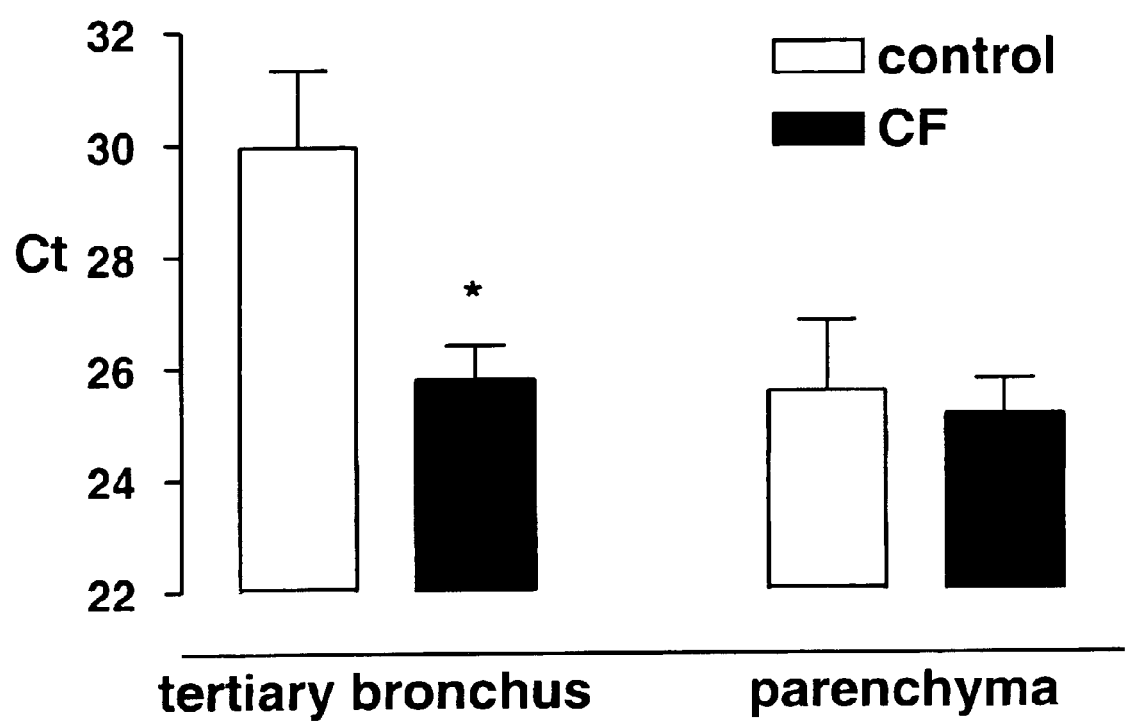
FIG. 2 shows differential expression of mRNA of the secretin receptor in control and CF lung regions. Ct refers to the fractional POR cycle number at which a PCR product is first detected as further described herein.

Agent which triggers anion efflux in respiratory tissue via the activation of a secretin receptor.

There are a number of mechanisms by which secretin receptors may be activated For example, expression of secretin is widely reported to be restricted to S-type enteroendocrine cells in the small intestine and colonic enteroendocrine cells and insulin producing β cells of the developing pancreas. Both enteroendocrine cells and pancreatic islets arise from the primitive embryonic gut endoderm. In addition, the primary airways are formed through a process termed branching morphogenesis, whereby 2 ventral lung buds sprout from the epithelium lining the floor of the embryonic foregut endoderm. Patterning of the airways is then accomplished by the outgrowth and repetitive branching of the two long buds. Pulmonary neuroendocrine (PNE) cells are amongst the first cells to differentiate from the primitive lung epithelium, and are generally most abundant in the airways of fetal and neonatal lungs. These cells are known to express a number of peptides including calcitonin, calcitonin gene related peptide, serotonin and endothelin, and can be visualized by their immunoreactivity to these peptides or to general endocrine markers such synaptophysin, chromogranin and protein gene product 9.5. In the CF bronchus, increased calcitonin immunoreactivity within endocrine cells has been demonstrated (Wolf et al, 1986).

We have found that there is increased chromogranin A immunoreactivity in CF tertiary bronchial sections compared to non CF lung, suggestive of an increased number of solitary endocrine cells in CF lung. Increased expression of endocrine cells within the tertiary bronchus of the CF lung would be expected to correlate with the increased presence of endocrine peptides including secretin. As such, direct or indirect stimulation of endocrine cells to locally release secretin (and/or secretin releasing peptides or peptides which exhibit affinity for the secretin receptor) within the lung would represent an alternative approach to stimulating the secretin receptor with exogenous secretin, or a mimetic and providing a therapeutic benefit in CF.

Further, the secretin gene may be upregulated by the provision of agents which increase the level of transcription of the gene, e.g. via promoter or enhancer regulation. The enhancer region of the secretin gene contains a cis-acting DNA consensus sequence (CAGCTG) known as an E box, which bind proteins belonging to the basic helix-loop-helix (bHLH) family of transcription factors. A bHLH protein known as BETA2/NeuroD has been demonstrated to lead to the tissue-specific regulation of secretin gene transcription (Mutoh et al, 1997). In knock out mice, BETA2/NeuroD deficient mice fail to develop enteroendocrine cells or pancreatic β cells, demonstrating the critical role of this transcription factor in the normal development of several specialized cells types that arise from the gut endoderm. Beta2/NeuroD expression has been demonstrated to locate only to endocrine cells in transgenic mice (Rhindi et al, 1999).

In addition, up regulation of endogenous secretin production may also be achieved by a variety of other methods known in the art (e.g. see Jiang et al., 2001; Yang et al., 1998; Morse et al., 2001; Lewis et al., 1997; West & Rodman, 2001, Alton & Kitson, 2000) including but not limited to gene therapy (delivery of DNA or RNA in a viral or non viral vector encoding a peptide capable of directly or indirectly stimulating the secretin receptor or its cell signaling pathway), or gene targeting (delivery of agents which target regulatory sequences or transcription factor binding sites on the promoter region of the gene encoding secretin or a related peptide, thereby switching on production of secretin or a related peptide capable of directly or indirectly stimulating the secretin receptor).

A number of mechanisms are known to stimulate secretin release, including the following:

Agents such as dibutyryl cyclic-3',5'-adenosine monophosphate, forskolin, 4 beta-12-O-tetradecanoylphorbol-13-acetate, the synthetic serine protease inhibitor, camostat, and the calcium ionophore, A2318, which stimulate $Ca^{2+}$ and cyclic-3', 5'-adenosine monophosphate-dependent secretin release (Xue et al, 1993);

Pancreatic phospholipase $A_2$ ($PLA_2$) which has been demonstrated to intrinsically possess secretin-releasing activity, which is independent of its digestive enzymatic activity (Chang et al, 1999);

The neuropeptides bombesin, gastrin releasing peptide, VIP and galanin have also been shown to modulate secretin release in secretin-producing cells (Chang et al, 1998); and Long chain fatty acids, such as sodium oleate are potent stimulators of secretin release from endocrine cells. Their stimulatory effect is potentiated by endogenous protein kinase A and mediated by activation of $Ca^{2+}$ influx through the L-type channels and of protein kinase C and $Ca^{2+}$/calmodulin-dependent protein kinase II (Chang et al, 2000).

Further, receptor activity modifying proteins, or RAMP are novel single transmembrane domain proteins that can modulate the expression and/or activity of at least two members of the secretin receptor GPCR family. To date there are 3 RAMP isoforms, 1–3, whose interactions are suggested to potentially result in trafficking of the receptor to the cell surface, modifying the degree of receptor glycosylation, and/or contributing to the ligand binding site through association with the receptor at the cell surface (Sexton, 1999).

RAMPS may indirectly alter a peptide selectivity for a specific receptor of the secretin GPCR family. For example, studies in which a single point mutation of the PTH receptor confers secretin responsiveness to this receptor, while the reverse mutation confers PTH responsiveness to the secretin receptor (Turner et al. 1996) has been suggested could be due to alterations in specific RAMP interactions with the receptor. (Sexton, 1999).

As such, agonism of the secretin receptor could be mediated via the simultaneous or sequential application of a peptide analogue or fragment of the secretin receptor family and a specific RAMP.

Respiratory tissue in which secretin receptors are activated particularly includes tissue within the distal regions of the lung selected from tertiary bronchus and lung parenchyma.

Secretin Receptor Ligand

As indicated above, the preferred secretin receptor ligand is human secretin (hSN). However other mammalian secreting, such as the closely related bovine, porcine or pig secretin, or canine, rodent, chicken and rabbit secretin (which exhibit various degrees of homology to human secretin) may be used, as well other naturally occurring or synthetic fragments or analogues of secretin, such as those identified herein.

Various other secretin receptor ligands are well known in the art. Many such ligands are based on the sequence of a natural secretin (e.g. human or porcine secretin) but contain from 1 to 7 (more usually from 1 to 5, and often 1, 2 or 3) amino acid substitutions or deletions, particularly but not exclusively in the N-terminal region.

For example, Gespach et al (1986) describe four synthetic secretin analogues including one corresponding to porcine secretin substituted at the N-terminus by sequence portions of vasoactive intestinal peptide (VIP), i.e. Ala4-Val5-pSN, together with Tyr1-Ala2-Glu3-pSN, Gln3-pSN, Phe1-Phe2-Trp3-Lys4-pSN (SEQ ID NO:13). Konig et al (1977) describe Ala4-pSN. Gardener et al (1976) describe the secretin fragment SN5-27 and three variants thereof, (9Gln-SN5-27, I5Asn-SN5-21 and 9Gln-I5Asn-5N5-27). 15-Lys-SN has also been described in the art (Gardener et al, 1979). Haffer et al (1991) describe eight secretin variants with reduced peptide bonds (the —CONH—bond being replaced by —CH2—HN—) between one of the eight N-terminal peptide bonds. Robberecht et al (1988) describe secretin fragments 2-27, 3-27, 5-27 and 7-27 and observed activity for secreting receptors. Konig et al (1986) exchanged the N-terminal 5 amino acids of a secretin for the N-terminal pentapeptide sequence of human somatotropin releasing factor to provide 1-Tyr-2,4-diAla-5-lle-SN, which showed secretin activity. Other active variants made were 3-L-Cystic acid-SN, 6-D-Phe-SN, 5-Allo-Thr-SN, and l-Cys-6-Cys-SN.

Further examples of secretin analogues which exhibit affinity for the secretin receptor include, [Ala4, Val5] and [D-Ala4, Val5]secretin, (D-Ala4) secretin; (D-Phe6) secretin; secretin 5–27, secretin 14–27 [Va15] secretin, [D-Ala4, Val5] secretin (Waelbroeck et al, 1981); substituted fragments such as [Gln9,Asn15] secretin (5-27) (Staun-Olsen et al, 1986); phenolic group containing analogues of porcine secretin including Nalpha-tyrosylsecretin, [Tyrl]secretin, and Nalpha-beta-(4-hydroxyphenyl) propionylsecretin (Yanaihara et al, 1977); carboxyl-terminal tricosapeptide analogues of secretin (S5-27) (9-Gln-S5-27, 15-Asn-S5-27), and 9-Gln-15-Asn-S5-27) (Gardne et al, 1976).

Vasoactive intestinal peptide (VIP), PACAP, glucagon, glucagon-like peptide and naturally occurring and synthetic analogues and fragments thereof, exhibit considerable homology to that of secretin. Examples of these include but are not limited, to (D-Ala4) VIP; (D-Phe4) VIP; (D-Phe2) VIP, fatty acyl derivatives of VIP, including myristyl-, palmityl- and stearyl-[Nle17]VIP (Gourlet et al, 1998), VIP 2-28; VIP 1-14; VIP 2-14; VIP 14-28; VIP 15-28; VIP 20-28; VIP 21-28, two sequences where the N-terminal VIP 1-6 or VIP 1-9 have been joined covalently with the C-terminal VIP 20-28 or VIP 21-28 (Couvineau et al, 1984); VIP 7-27, VIP 11-28, VIP 1-22-NH$_2$, VIP 16-28 (Staun-Olsen et al, 1986), VIP [10-28] and VIP [16-28]. Analogues of secretin and VIP, referred to as the vasectrins, have also been described by Beyerman et al, 1981. PACAP (1-27; 1-38) and analogue examples include PACAP(1-23, VIP-24-28), PACAP(1-24,Cys-25), PACAP(1-23), PACAP(3-27), PACAP(1-19), PACAP(3-19), PACAP(1-12), and PACAP (18-38) (Schmidt et al, 1993), Glucagon, and GLP-1, and their related analogues and fragments include GLP-1 (7-37) GLP-1-(1-37) amide, -(6-37) amide, -(8-37) amaide, -(7-36) amide (Suzuki et al, 1989), those with alterations in the N-terminal position 1 including N-methylated- (N-me-GLP-1), alpha-methylated (alpha-me-GLP-1), desamidated- (desamino-GLP-1) and imidazole-lactic-acid substituted GLP-1 (imi-GLP-1). (Callwitz et al, 2000).

The secretin receptor ligands described in the above literature, which is incorporated herein by reference, may all be used in the present invention, though those of skill in the art will appreciate that the above-cited references are not exhaustive and other secretin receptor ligands may be used.

The suitability of candidate ligands may be determined experimentally. For example, Charlton et al (1983) report that secretin injected intracerebroventricularly significantly increased defecation and decreased novel-object approaches in rats, but showed no significant effects on stereotypic behaviour. Such a test may be performed in rats with a secretin receptor ligand to determine its suitability for the present invention (i.e. those ligands which show similar effects via agonism of the secretin receptor may be selected).

Secretin is available from commercial sources (e.g. Peninsula Laboratories Inc, USA) or it and the above-described ligands may be obtained by reference to readily available published literature.

Compositions of the Invention

The novel findings reported herein give rise to novel compositions which comprise a secretin receptor ligand together with at least one other compound active against CF or COPD.

In the case of CF, such compounds include mucolytic agents such as acetylcysteirie, deoxyribonuclease I (dornase) or erdosteine, as well as other anti-CF agents such as nedocromil or ibuprofen.

In the case of COPD, such compounds include bronchodilators such as theophylline, ipratropium, beta 2 agonists such as salbutamol or salmeterol or anti-inflammatory agents such as steroids.

The amount of secretin receptor ligand in such a composition may be, for example, from 1% to 99% by weight of the total amount of active ingredients (i.e. excluding carriers or diluents), for example from 10% to 90% by weight.

In a related aspect, the present invention provides a combination of a secretin receptor ligand and a second compound active against CF or COPD for simultaneous or sequential use in the treatment of CF or COPD respectively. By "simultaneous" it is meant that the two compounds are administered at the same time, though not necessarily in the same composition. By "sequential" it is meant that the two compounds are administered within a time period such that the first of the two compounds is still active in the patient when administration of the second of the two compounds occurs. Preferably, "sequential" means within the same 24 hour, preferably within the same 12 hour, such as within the same 6, 3, 1, half or quarter hour time period.

Formulation and Administration

Treatment of patients in accordance with the present invention may be performed by administering to a patient a secretin receptor ligand in the form of a pharmaceutical composition, either with or without a further active ingredient present (reference below to compositions will be understood to include both types, though for brevity only the secretin receptor ligand is specifically mentioned). The composition may be in combination with a non-toxic, pharmaceutically acceptable carrier, In this context the invention also covers a method of treating CF comprising administering a therapeutically effective amount of the secretin receptor ligand of this invention or a composition of this invention on a patient to be treated.

In clinical practice the compositions of the present invention may be administered parenterally due to the fact that being a peptide the hormone is sensitive to biologically active environments. Oral or rectal administration may, however, be conceivable, for example using compositions of the slow release type making it possible for the active ingredient to reach the site of primary interest, namely the tertiary bronchus.

Secretin receptor ligands may be formulated in a suitable form for administration by inhalation (e.g. via an aerosol) or insufflation (either through the mouth or nose), or by parenteral administration (introduced by routes other than intestinal routes).

Delivery of proteins or peptides via inhalation may be accomplished using liquid or solid preparations of the secretin receptor ligand. Thus the invention contemplates formulations comprising secretin receptor ligand for us in a wide variety of devices that are designed for the delivery of pharmaceutical compositions and therapeutic formulations to the respiratory tract. In one aspect of the present invention, secretin receptor ligand is administered in aerosolized or inhaled form. The secretin receptor ligand, combined with a dispersing agent, or dispersant, can be administered in an aerosol formulation as a dry powder or in a solution or suspension with a diluent.

Suitable dispersing agents are well known in the art, and include but are not limited to surfactants and the like. Surfactants are generally used in the art to reduce surface induced aggregation of protein caused by atomization of the solution forming the liquid aerosol. Examples of such surfactants include polyoxyethylene fatty acid esters and alcohols, and polyoxyethylene sorbitan fatty acid esters. Amounts of surfactants used will vary, being generally within the range of about 0.001 to 4% by weight of the formulation. In a specific aspect, the surfactant is polyoxyethylene sorbitan monooleate or sorbitan trioleate.

The liquid aerosol formulations contain the secretin receptor ligand and a dispersing agent in a physiologically acceptable diluent. The dry powder aerosol formulations of the present invention consist of a finely divided solid form of the secretin receptor ligand and a dispersing agent, and optionally a bulking agent, such as lactose, sorbitol, sucrose, or mannitol, and the like, to facilitate dispersal of the powder. With either the liquid or dry powder aerosol formulation, the formulation must be aerosolized. That is, it must be broken down into liquid or solid particles in order to ensure that the aerosolized dose actually reaches the bronchii and/or alveoli, as desired. In general the mass median dynamic diameter will be 5 micrometers ($\mu$m) or less in order to ensure that the drug particles reach the lung bronchii or alveoli (Wearley et al 1991)

With regard to construction of the delivery device, any form of aerosolization known in the art, including but not limited to nebulization, atomization or pump aerosolization of a liquid formulation, and aerosolization of a dry powder formulation, can be used in the practice of the invention. A delivery device that is uniquely designed for administration of solid formulations is envisioned. Often, the aerosolization of a liquid or a dry powder formulation will require a propellant. The propellant can be any propellant generally used in the art. Examples of useful propellants include chlorofluorocarbons, hydrofluorocarbons, hydrochlorofluorocarbons, and hydrocarbons, including trifluoromethanet dichlorodifluoroethane, dichlorotetrafluoroethanol, and 1,1,1,2-tetrafluoroethane, and combinations thereof.

In a preferred aspect of the invention, the device for aerosolization is a metered dose inhaler. A metered dose inhaler provides a specific dosage when administered, rather than a variable dose depending on administration. Such a metered dose inhaler can be used with either a liquid or a dry powder aerosol formulation.

Systems of aerosol delivery, such as the pressurized metered dose inhaler and the dry powder inhaler are disclosed in Newman, Aerosols and the Lung, Clarke, S. W. and Davia, D. editors, pp 197–22 and can be used in connection with the present invention.

Additional pharmaceutical methods may be employed to control the duration of action of the antagonists of this invention. The antagonists also may be entrapped in microcapsules prepared, for example, by coacervation techniques by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Osol, A., ed (1980).

For intranasal administration, the secretin receptor ligands may be formulated as solutions for administration via a suitable metered or unit device or alternatively as a powder mix with a suitable carrier for the administration using a suitable delivery device. Alternatively, secretin receptor ligands could be delivered transnasally in a similar fashion.

For example, preparation of secretin for transnasal administration has been described in JP60123426.

Preparations for parenteral administration includes sterile aqueous or non-aqueous solutions, suspensions or emulsions. Examples of non-aqueous solvents or suspending media are propylene glycol, vegetable oils, such as olive oil, and injectible organic esters, such as ethyl oleate. These compositions may also contain adjuvants, such as preserving, wetting, emulsifying and dispersing agents. They may be sterilized, for example, by filtration through a bacteria-retaining filter, by incorporation of sterilizing agents in the composition, by irradiation or by heating. They may be also be manufactured in the form of sterile solid compositions, which can be dissolved in a sterile injectible medium immediately before use. As well as the more customary intravenous and intramuscular routes the compositions may also be administered by intraarticular injection.

The percentages of active ingredient in the compositions of the invention may be varied as long as they constitute a proportion such that a suitable dosage for the desired stimulatory effect on the pancreas is obtained. Obviously several unit dosage forms may be administered at about the same time. Generally, the compositions should contain from about 0.1% to about 80% by weight of active ingredient.

The dose employed depends upon the desired stimulatory effect, the route of administration and the duration of the treatment. Typical doses may be in the range of from $10^{-8}$ to $10^{-3}$ mg per day, preferably from $10^{-6}$ to $10^{-4}$ mg per day for a human patient. The secretin receptor ligand may be administered each day or, according to the wishes of the medical practitioner, less often, e.g. weekly, or until the desired therapeutic effect is achieved.

The following examples illustrate the invention.

EXAMPLE 1

RNA Expression Profiles

Messenger RNA expression profiles of the secretin receptor (protein accession P47872; nucleotide accession U28281) was examined. Total RNA was isolated from tertiary/quaternary bronchus and lung parenchyma from 5 control and 5 CF donors using TriZol™ a commercially available solution of phenol and guanidine isothiocyanate, according to the protocol described by the manufacturer (Life Technologies). Samples of RNA were used only if intact 18s and 28s ribosomal RNA were detected by gel electrophoresis and if genomic DNA formed less than 10% of the total nucleic acid sample. Total RNA samples were annealed to the primer probe sequence plus a glyceraldehyde-3-phosphate dehydrogenase (GAPDH; accession no. P04406) primer and reverse transcribed using MuLV reverse transcriptase. Quantitative sequence detection was carried out on the resulting cDNA.

The applicants have developed protocols for quantitative analysis of mRNA expression using the ABI prism 7700 Sequence Detection System (Perkin Elmer). Details of the system are set out in WO00/05409. In brief, the system uses fluorogenic probes to generate sequence specific fluorescent signals during PCR. The probes are oligonucleotides with fluorescent reporter and quencher dyes attached. While a probe is intact, the intensity of reporter fluorescence is suppressed by a quencher. When a probe forms part of a replication complex during the PCR process, the quencher is separated from the reporter dye resulting in a increase in fluorescence which is then detected by the ABI 7700 sequence detector. The ABI 7700 has a built in thermal cycler, and a laser directed at each of the 96 sample wells via bi-directional fibre optic cables. Emitted fluorescence through the cables to a detector where emissions which fall between 520 nm and 660 nm are collected every few seconds. The system software analyses the contribution of each component dye to the experiment spectrum, and normalizes the signal to an internal reference dye. The peaks of these normalised 'reporter' values (Rn) are then plotted against thermal cycle number to produce an amplification plot—to allow visualisation of the extent of PCR product generation.

The starting copy number of a target sequence (Cn) is established by determining the fractional PCR cycle number (Ct) at which a PCR product is first detected—the point at which the fluorescence signal exceeds a threshold baseline. Therefore the lower a Ct value the greater the Cn. Quantification of the amount of target mRNA in each sample is established through comparison of the experimental Ct values with standard curves for the target sequence which are constructed during each experiment.

Primer probe sets were specifically designed for the detection of secretin receptor mRNA. Off-line homology searches revealed no significant matches with gene sequences logged at Genbank. Forward and reverse primer and probe sequences for the secretin receptor were as follows:

```
Forward  GACCAGCATCATCTGAGAGGCT    (SEQ ID NO:1)

Reverse  CCTTCGCAGGACCTCTCTTG      (SEQ ID NO:2)

Probe    TCTCTGTCCGTGGGTGACCCTGCT  (SEQ ID NO:3)
```

GAPDH primer probe sets were as follows

```
Forward  GAAGGTGAAGGTCGGAGTCAAC    (SEQ ID NO:4)

Reverse  CAGAGTTAAAAGCAGCCCTGGT    (SEQ ID NO:5)

Probe    TTTGGTCGCGTATTGGGCGCCT    (SEQ ID NO:6)
```

Reaction conditions were optimised using genomic DNA as a template and a primer probe concentration grid followed by a probe concentration gradient experiment. Primer concentrations were selected to give the most efficient amplification of gene product, i.e. those which generate a low threshold cycle and a relatively high accumulation of fluorescence. These optimal primer concentrations were then used to select the optimum probe concentration.

A respiratory disease association of the secretin receptor was demonstrated by profiling secretin receptor mRNA expression in the tertiary bronchus and parenchyma from up to 5 fully consented donors pathologically and histologically diagnosed with the following respiratory disorders: non-smoker control, smoker, asthmatic, cystic fibrosis, pneumonia, emphysema, chronic obstructive pulmonary disease (COPD). CP lung tissue was obtained by full consent from 5 patients undergoing heart and lung transplants.

Figure 3:
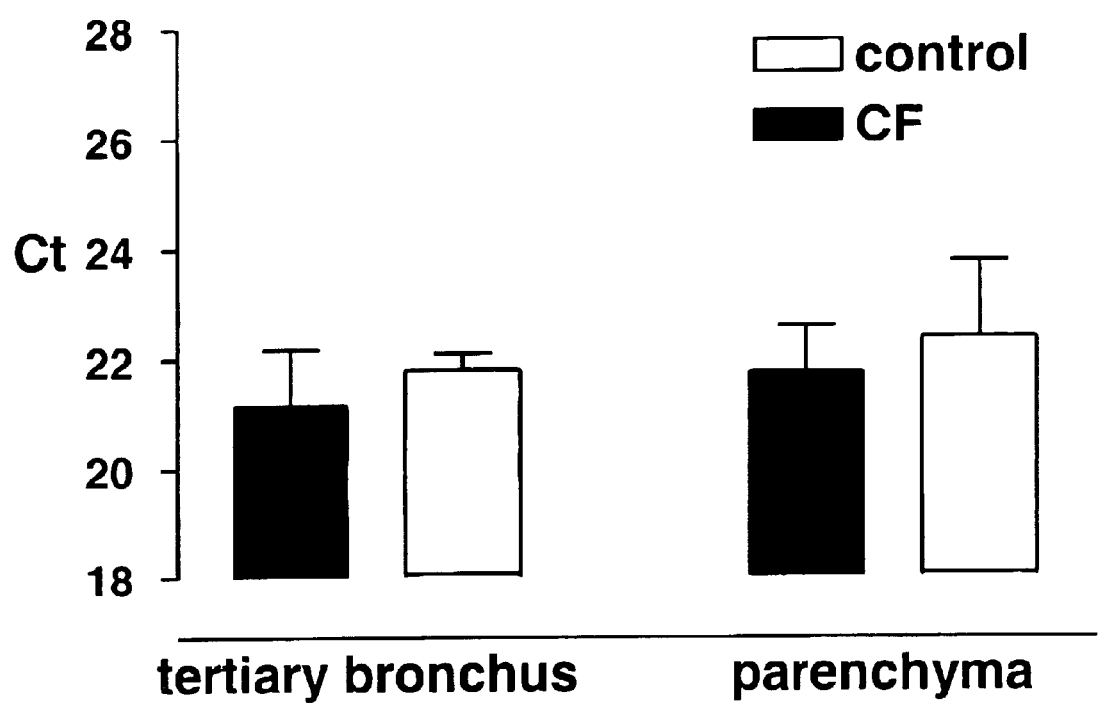
FIG. 3 shows mRNA expression of GAPDH in control and lung CF regions. Ct is defined above.

FIG. 2 shows the differential mRNA expression of the secretin receptor in control and CF lung regions, illustrating increased expression of the secretin receptor in CF tertiary bronchus. Data are representative of the mean±s.e.m QRT-PCR threshold cycle from 5 control and 5 cystic fibrosis tissue donors in each lung region. * p=0.0246 denotes statistical significance derived from an unpaired Students T-test. As a control, FIG. 3 shows mRNA expression of GAPDH in control and CF lung regions. Data are representative of the mean±s.e.m QRT-PCR threshold cycle from 5 control and 5 cystic fibrosis tissue donors in each lung region. No statistical differences were observed within or between groups.

Decreased secretin receptor expression was demonstrated in the lung parenchyma of 5 COPD donors in comparison to 5 control donors (p=0.0465). However no other donor groups exhibited differences in the expression of secretin receptor mRNA.

In all cases, however, the observation of secretin receptor expression at any level in tissues of the distal regions of the lung is novel and provides the underlying basis for the present invention.

Figure 4:
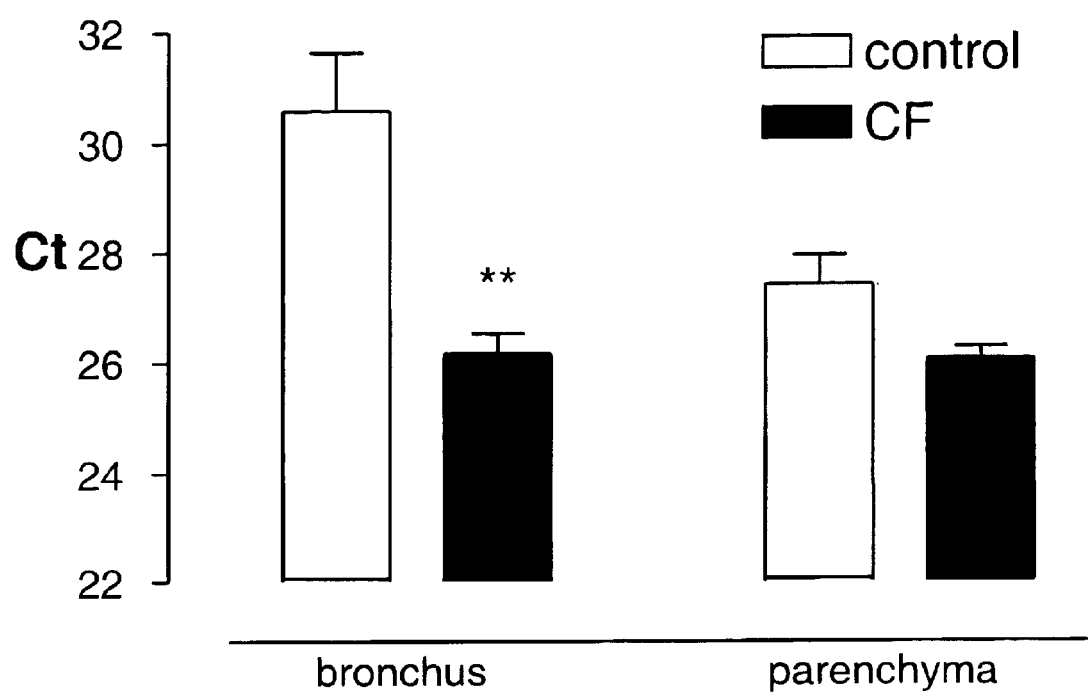
FIG. 4 shows differential expression of mRNA of the secretin receptor in control and CF lung regions from a sample of 16 control and 25 CF tissue donors. Ct is defined above.

FIG. 4 shows the results of a subsequent expression study carried out with tissue derived from 25 CF donors and 16 non-smoking control donors. Data are representative of the mean ±s.e.mean QRT-PCR threshold cycle from 25 CP donors and 16 non-smoking control donors in each lung regions. ** p=0.009 denotes statistical significance derived from two-way analysis of variance. The results obtained were similar to those obtained in FIG. 2, i.e. significantly increased expression of the secretin receptor in CF tertiary bronchus compared to control, with both groups having similar levels of expression in the parenchyma.

The data provided by Example 1 provides the underlying bais for the present invention. That is, impaired $Cl^-$ efflux from cells in the respiratory tract into the airway lumen represents the etiological problem in CF. However, this loss of the $Cl^-$ channel and ion movement also impairs bicarbonate ($HCO_3^-$) secretion from cells and enhances sodium ion ($Na^+$) reabsorption into cells, via epithelial, amiloride-sensitive $Na^+$ channels.

The lavage of the healthy lung consists primarily of $H_2O$ (approx. 95%), with luminal $HCO_3^-$ maintaining secreted proteins such as mucus and digestive enzymes in a soluble, inactive state. However, CF airway epithelia exhibit abnormally high rates of surface liquid absorption due to the high intracellular concentrations of $Na^+$ and $Cl^-$ and therefore patients have a very low moisture content within their airways. Together this leads to significant thickening of the mucus, and subsequent impairment of the mucociliary clearance from the CF lung.

Movement of $HCO_3^-$ across apical membrane of lung epithelial cells occurs predominantly via an electrogenic $Cl^-/HCO_3^-$ exchanger, with water crossing hydrophobic plasma membranes either by simple osmotic diffusion or through a facilitative transport mechanism mediated by members of a family of aquaporin (AQP) water channel proteins. Currently it is thought that $HCO_3^-$ and $Cl^-$ are predominantly involved in the osmotic movement of $H_2O$.

Based on the physiological role of secretin and its receptor in ionic regulation in the duodenum and pancreas, the applicants suggest, based on the present findings, that increased mRNA and functional expression of the secretin receptor may represent the human body's evolutionary, pathophysical response in order to compensate for the defect in the CFTR. As secretin peptide synthesis occurs in the duodenum, secretin receptors within the lung will not be exposed to the secretin peptide. While not being bound by any one particular theory, it is proposed that agonism of the secretin receptor by pharmacological intervention will treat the underlying biochemical respiratory problems associated with CF by all or some of the following:

(a) Stimulating $Cl^-$ efflux via cAMP-dependent activation of $Cl^-$ channels from respiratory cells of the tertiary bronchus. Secretin receptor stimulation or forskolin-mediated increases in cAMP have been shown to stimulate a small, single channel $Cl^-$ selective conductance, of about 4 pS across the apical membrane of rat pancreatic duct cells (Gray et al, 1988). Although secretin has been demonstrated to stimulate the CFTR and $Cl^-$ efflux across the apical membranes of non-CF human epithelial cells (e.g. gallbladder; Dray-Charier et al, 1995), this $Cl^-$ conductance is reported to be 6–12 pS. Therefore this $C^-$ represents an alternative cAMP-dependent $Cl^-$ conductance.

(b) Stimulated increases in cAMP, activating protein kinases, and leading to the phosphorylation and subsequent regulation of epithelial $Na^+$ channels or $Na^+\text{-}K^+$-ATPases in respiratory cells, thereby reducing $Na^+$ reabsorption and stimulation of lung liquid movement, Such a mechanism has been demonstrated in the rat alveolar epithelial cells with cAMP coupled beta-adrenergic receptor stimulation (Minakata et al, 1998).

(c) Subsequently increased luminal levels of $Cl^-$ will act as a substrate for the secretin activated $Cl^+/HCO_3^-$ exchanger, allowing the electrogenic movement of $HCO_3^-$ into the airway lumen. Secretin has been widely demonstrated to stimulate the activity of $Cl^-/HCO_3^-$ exchanger which is functionally coupled with a cAMP-dependent Cl— channel (CFTR) on the apical epithelium (for example in bile duct epithelial cells, Alvaro et al, 1993; 1997). This ionic movement mediated by secretin has been demonstrated to stimulate electrogenic $Na^+/HCO_3^-$ cotransport, leading to correction of intracellular pH (Ishiguro et al, 1993).

(d) Additionally, increased $HCO_3^-$ levels are known to maintain secreted proteins in mucus in a soluble, inactive state (Lee et al, 1999).

(e) Induce the translocation and insertion of AQPs into the plasma membrane, allowing the movement of water into the lumen of the airways. In rat cholangiocytes, secretin has been demonstrated to cause a 60% concentration dependent increase in osmotic $H_2O$ permeability by inducing the translocation of AQP-1 water channels (Marinelli et al, 1997). This process will also be assisted by the osmotic diffusion of $H_2O$ across the plasma membrane, due to the correction of $Na^+$, $Cl^-$, $HCO_3^-$ and pH via the previously described mechanisms, in bronchial cells and the airway lumen.

In support of these proposals, we investigated the action of secretin on tertiary bronchus tissue samples.

EXAMPLE 2
Functional Activity of Secretin Receptor in Tertiary Bronchus

Functional activity of the secretin receptor was examined in the tertiary bronchus and in epithelial cells derived from the tertiary bronchus of normal tissue.

In brief, non-branching regions of the human tertiary bronchus from non-CF donors were dissected, cut longitudinally and mounted in between the two compartments of a modified Ussing chamber to measure the short circuit current across the bronchial wall. Both luminal (airway) and basolateral membranes were bathed in oxygenated Krebs extracellular solution and the tissue voltage clamped to zero to allow changes in short circuit current in response to secretin to be measured. Amiloride at a concentration of 10 $\mu$M was initially added to the luminal membrane (FIG. 5, point a)(as described by those in the art) to partially block the predominant sodium ion current and unmask underlying ionic currents. On attainment of a stable base line, 3 $\mu$M human secretin (supplied by Sigma, catalogue number S714) was added to the luminal membrane (FIG. 5, point b).

Figure 5:
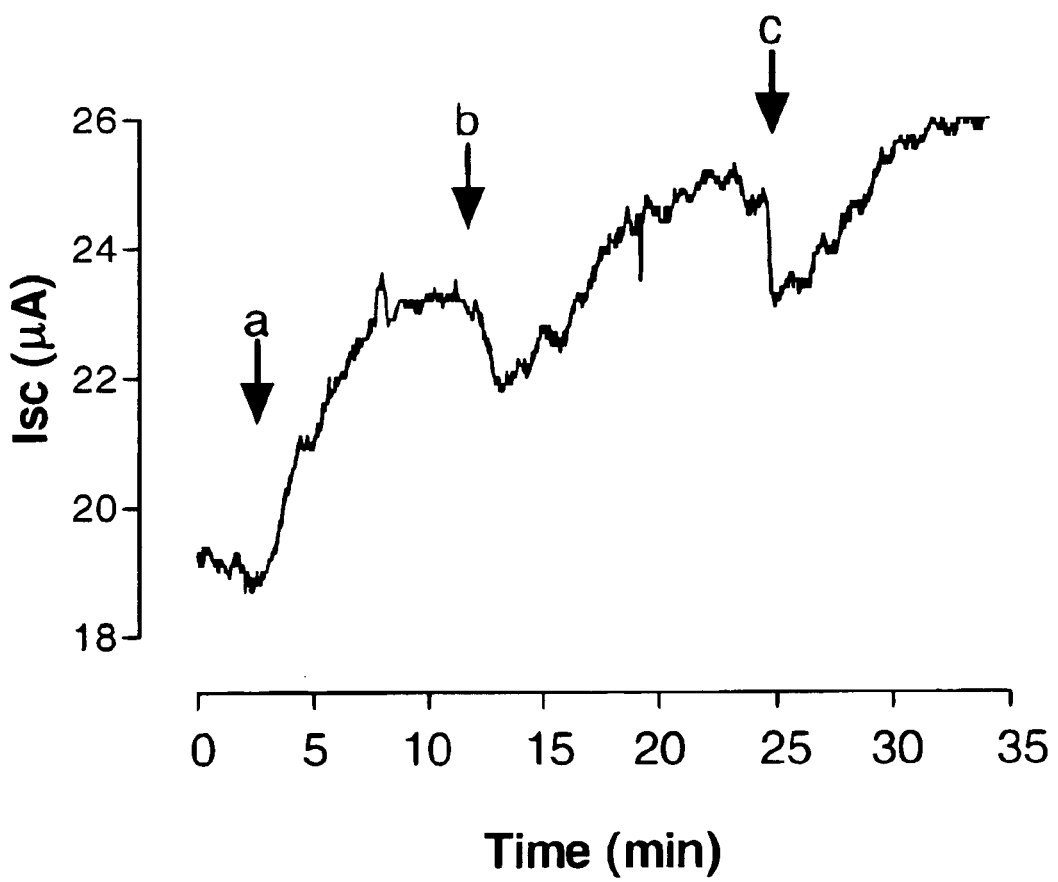
FIG. 5 shows that secretin stimulates ionic movement in the non-CF tertiary bronchus. Time points "a", "b" and "c" are described further in Example 2.

Secretin was found to stimulate ionic movement in a manner consistent with the movement of a negatively charged ion ($Cl^-$ and/or $HCO_3^-$ (FIG. 5). Like secretin, addition of 10 $\mu$M ATP or UTP to the apical membrane of the lung epithelium (FIG. 5, point c) was demonstrated to stimulate a similar ionic movement of similar magnitude. These ATP and UTP mediated effects are widely reported in the literature to be due to the stimulation of a $Ca^{2+}$-activated $Cl^-$ current via the P2Y2 purinoceptor. Both described agonists, at high concentrations produced responses of a similar magnitude.

Figure 6:
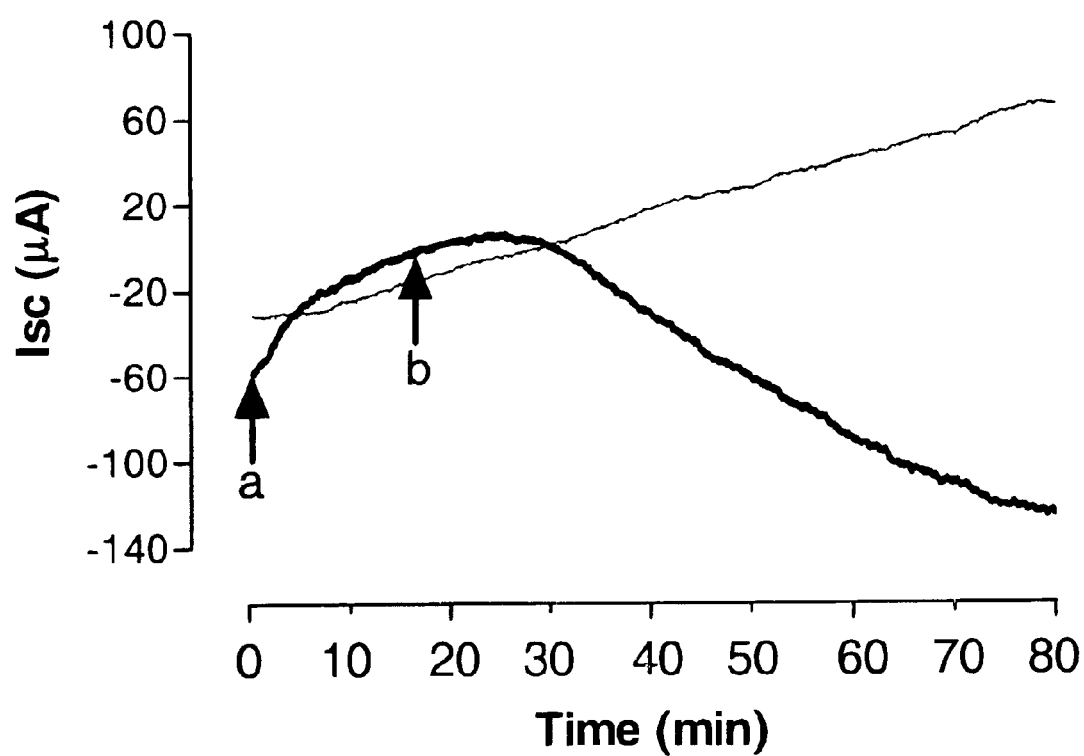
FIG. 6 shows that secretin stimulates non-CTFR dependent ionic movement in confluent monolayers of primary human tertiary bronchial epithelial cells derived from non-CF donors. Time points "a" and "b" are further described in Examole 2.

Functional effects of the secretin receptor were probed in epithelial cells derived from the human tertiary bronchus. In brief, tertiary bronchial epithelial were isolated by overnight protease digestion and then cultured until confluency on Snapwell (Costar) permeable supports. The supports were mounted in a modified Ussing chamber, and both luminal and basolateral membranes were bathed in oxygenated Krebs extracellular solution. The cells were voltage clamped to zero to allow changes in short circuit current Isc in response to secretin to be measured. As previously described, 10 $\mu$M amiloride was initially added to the luminal membrane (FIG. 6, point a)followed by the addition of 100 $\mu$M secretin to the luminal membrane (FIG. 6, point b). A time matched, amiloride-treated control is denoted by the thin trace. Consistent with observations in the tertiary bronchus, secretin stimulated ionic movement in a manner consistent with the movement of a negatively charged ion (Cr and/or $HCO_3$). Furthermore, addition of 500 $\mu$M glibenclamide, a recognised inhibitor of the CFTR failed to suppress secretin mediated ionic movement, suggestive that a similar ionic movement would be observed in CF tertiary bronchial epithelial cells.

EXAMPLE 3
Stimulation of Ionic Movement in CF Bronchus

Figure 7:
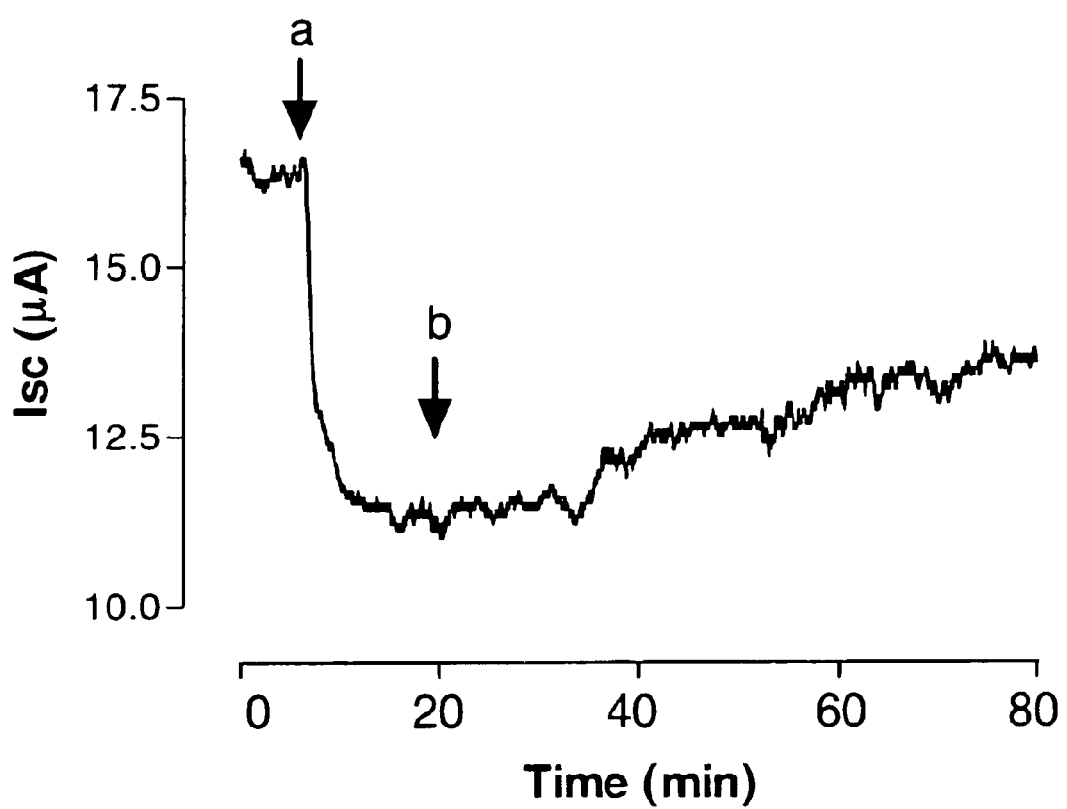
FIG. 7 shows that secretin stimulates ionic movement in the human CF tertiary bronchus. Time Points "a" and "b" are described in Example 3.

The experiment described above was repeated using human CF tertiary bronchus, using 1 $\mu$M secretin. The result obtained is shown in FIG. 7, At point (a), addition of amiloride blocks the underlying sodium current. Addition of 1 $\mu$M secretin at point (b) stimulates ionic movement of a negatively charged ion, confirming the experimental observations in the non-CF bronchus.

Figure 8:
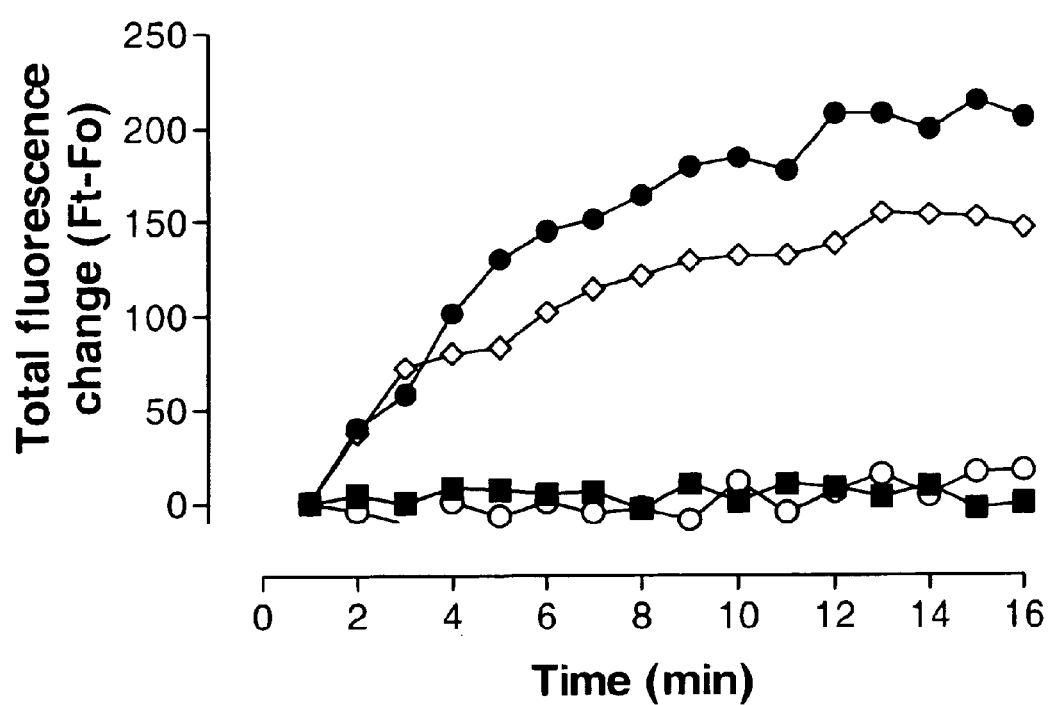
FIG. 8 shows the effect of secretin on chloride ion efflux in primary human tertiary bronchial epithelial cells derived from non CF donors. A detailed description of the samples is Provided in Example 4.

EXAMPLE 4
Stimulation of Chloride Ion Efflux by Secretion in Tertiary Bronchus Ionic movement in tertiary bronchial epithelial cells was further characterised with the use of the $Cl^-$ specific fluorescent probe MQAE (n-(ethoxycarbonylmethyl)-6-methoxyquinolinium bromide; Molecular Probes). In brief, primary human, tertiary bronchial epithelial cells were isolated as previously described and cultured in a 96 well plate. On reaching confluency, cells were loaded overnight with 4 mM MQAE. Cells were washed in a chloride containing HEPES buffer, before passive $Cl^-$ efflux was initiated by the addition of a $Cl^-$ free buffer. Addition of nanomolar concentrations of secretin stimulated $Cl^-$ efflux, as determined by changes in MQAE fluorescence. Secretin mediated changes in fluorescence were abolished by the addition of the non-selective $Cl^-$ channel blocker NPPB (5-nitro-2-(3-phenylpropyl-amino)benzoic acid; 100 $\mu$M). The results are shown in FIG. 8 which shows the effect of secretin at two concentrations (open diamonds 12.5 nM; closed circles 100 nM). 100 nM Secretin mediated $Cl^-$ efflux was inhibited by the non-selective $Cl^-$ blocker NPPB (open circles). Unstimulated $Cl^-$ efflux is demonstrated by the closed squares.

EXAMPLE 5
Chromogranin a Immunoreactivity in CF Tertiary Bronchus

Cryostat section (5–7 $\mu$m) were cut from paraformaldehyde fixed, paraffin embedded sections of 5 CF and 3 non-CF tertiary bronchus, and stained with a mouse monoclonal chromogranin A antibody (Vector Laboratories Ltd; cat. No. NCL-CHROM), followed by IgG secondary antibody. The vector Universal Elite ABC kit was used to detect antibody binding. Adjacent sections were incubated with a no primary negative control and appeared free of non specific binding. In CF tissue stained with the cromogranin A antibody, a number of solitary endocrine cells were observed, compared to little or no staining the the normal tissue and controls. This indicates the presence of S-type enteroendocrine cells which are a target for modulators of secretin expression. Thus agents which stimulate secretin production in such cells may be used in the treatment of CF.

EXAMPLE 6
Endogenous Regulation of Secretin Production

The mRNA expression of NeuroD in the tertiary bronchus and lung parenchyma in 17 normal and 25 CF lung donors was examined. Primer probe sets were specifically designed for the detection of NeuroD (accession number BAA76603). Off line homology searches revealed no significant matches with gene sequences logged at Genbank. Forward and reverse primer and probe sequences for the transcription factor BETA2/NeuroD were as follows:

| | | |
|---|---|---|
| forward primer | GAACGCGGCGCTAGACA | (SEQ ID NO:7) |
| reverse | GTCTCGATTTTGGACAGCTTCTG | (SEQ ID NO:8) |

```
                    -continued
primer
probe      AGCAAGGCACCACCTTGCGCA       (SEQ ID NO:9)
```

Figure 9:
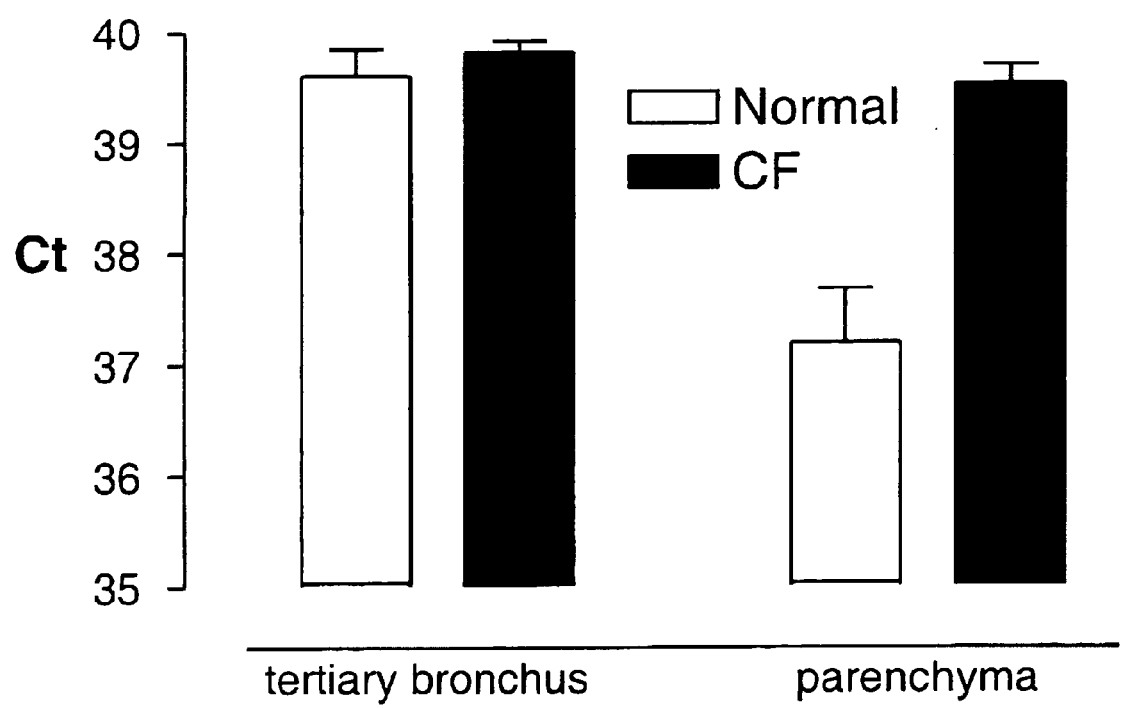
FIG. 9 shows the levels of NeuroD mRNA in tertiary bronchus and lung parenchyma of CF patients. Ct is defined above.

Data (FIG. 9) are expressed as mean±s.e.mean of the QRT-PCR threshold cycle, whereby the higher the threshold cycle, the lower the copy number of the gene per 100 ng tRNA.

A significant reduction in NeuroD mRNA expression was observed in the CF parenchyma, with similar low abundance levels present in the tertiary bronchus of both control and CF donors. Functionally, this reduction in NeuroD in the CF parenchyma may correlate with a decreased regulation and synthesis of endogenous secretin. Enhancement of the functional expression of NeuroD may therefore lead to an enhancement in the endogeous levels of secretin within the lung, and therefore an indirect mechanism for the treatment of cystic fibrosis using agonism of the secretin receptor.

In summary, stimulation of the secretin receptor may be used to correct the ionic and $H_2O$ problems of CF, reducing the thickness of the mucus layer, and allowing mucociliary clearance from the lung.

References

Alton E, Kitson C. (2000) Gene therapy for cystic fibrosis. Expert Opin Investig Drugs. 9; 1523–35. Review Alvaro. D., Cho, W. K., Mennone, A. & Boyer, J. L. (1993) Effects of secretin on intracellular pH regulation in isolated rat bile duct epithelial cells. *J. Clin. Invest.* 92; 1314–1325.

Alvaro, D., Gigliozzi, A., Fraioli, F., Romeo, R., Papa, E., Delle, Monache, M & Capocaccia, L. (1997) Hormonal regulation of bicarbonate secretion in the biliary epithelium. *Yale J. Biol.* 70; 417–426.

Beyerman, H. C., Buijen van Weelderen, A. W., Chang, T. M., Chey, W. Y., Grossman, M. I., Kranenburg, P., Scratcherd, T., Solomon, T. E., Voskamp, D. (1981) Synthesis, biological and immunochemical properties of analogues of secretin and vasoactive intestinal peptide (VIP): the vasectrins. *Life Sci.* 29:895–902

Chang, C. H., Chey, W. Y., Chang, T. M. (2000). Cellular mechanism of sodium oleate-stimulated secretion of cholecystokinin and secretin. Am. J. Physiol. Gastrointest. Liver. Physiol. 279:G295–303

Chang, C. H. Chey, W. Y., Erway, B., Coy, D H, Chang T M (1998). Modulation of secretin release by neuropeptides in secretin-producing cells. *Am J Physiol* 275; G192–202

Chang, T., Chang, C. H., Wagner, D. R. & Chey, W. (1999) Porcine Pancreatic Phospholipase $A_2$ Stimulates Secretin Release from Secretin-producing Cells. *J. Biol. Chem.* 274; 10758–10764

Charlton, C. G., et al (1983) Secretin modulation of behavioural and physiological functions in the rat. *Peptides*, 4; 73942.

Couvineau, A., Rouyer-Fessard, C., Fournier, A., St Pierre, S., Pipkorn, R., Laburthe, M. (1984) Structural requirements for VIP interaction with specific receptors in human and rat intestinal membranes: effect of nine partial sequences. *Biochem Biophys Res Commun.* 121:493–8

Dray-Charier, N., Paul, A., Veissiere, D., Mergy, M., Scoazec, J. Y., Capeau, J., Brahimi-Horn, C. & Housset, C. (1995) Expression of cystic fibrosis transmembrane conductance regulator in human gallbladder epithelial cells. *Lab Invest* 73; 828–836.

Fortner, C. N., Lorenz, J. N. & Paul, R. J. (2001) Chloride channel function is linked to epithelium-dependent airway relaxation. Am. J. Physiol. Lung Cell Mol Physiol. 280; L334–L341

Gallwitz, B., Ropeter, T., Morys-Wortmann, C., Mentlein, R., Siegel, E. G., Schmidt, W. E. (2000) GLP-1-analogues resistant to degradation by dipeptidyl-peptidase IV in vitro. *Regul Pept* 86; 103–11

Gardner, J. D., Conlon, T. P., Fink, M. L., Bodanszky, M. (1976) Interaction of peptides related to secretin with hormone receptors on pancreatic acinar cells. *Gastroenterology* 71:965–70

Gardner, J. D., Rottman, A. J., Natarajan, S. & Bodansky, M. (1979) Interaction of secretin 5-27 and its analogues with hormone receptors on pancreatic acini. *Biochim Biophys Acta.* 583; 491–503.

Gespach, C., Bataille, D, Vauclin, N., Moroder, 1., Wonsch, E. Rosselin, G. (1986) Secretin receptor activity in rat gastric glands. Binding studies, cAMP generation and pharmacology. Peptides 7; 155–163

Gourlet, P., Rathé, J., De Neef, P., Cnudde, J., Vandermeers-Piret, M. C., Waelbroeck, M., Robberecht, P. (1998) Interaction of lipophilic VIP derivatives with recombinant VIP1/PACAP and VIP2/PACAP receptors. Eur J Pharmacol. 354; 105–11

Gray, M. A., Greenwell, J. R. & Argent, B. E. (1988) Secretin-regulated chloride channel on the apical membrane of pancreatic duct cells. *J Memb Biol.* 105; 131–142.

Haffer, B. M., Hocart, S. J., Coy, D. H., Mantey, S., Chiang, H. C. & Jensen, R. T. (1991) Reduced peptide bond pseudopeptide analogues of secretin. A new class of secretin receptor antagonists. *J. Biol. Chem.* 266; 316–322.

Ishiguro, H., Steward, M. C., Lindsay, A. R. & Case, R. M. (1996) Accumulation of intracellular $HCO_3^-$ by $Na^+/HCO_3^-$ cotransport in interlobular ducts from guinea-pig pancreas. *J. Physiol.* 495; 169–178.

Jiang J G, Johnson C, Zarnegar R. (2001) PPAR gamma-mediated transcriptional upregulation of the hepatocyte growth factor gene promoter via a novel composite cis-acting element. *J Biol Chem.* Apr 5.

Konig, W., Bickel, M., Karch, K., Teetz, V. & Uhmann. (1984) Analogues and fragments of secretin. *Peptides* 5; 189–193.

Konig, W., Bickel, Wissmann, H., Sandeur, J. (1986) New analogues of secretin. Peptides 7; 61–67

Konig et al (Gastroenterology, 1977, 72;797–800)

Lee, M. G., Wigley, W. C., Zeng. W., Noel, L. E., Marino, C. R., Thomas, P. J. & Muallem, S. (1999) Regulation of $Cl^-/HCO_3^-$ exchange by cystic fibrosis transmembrane conductance regulator expressed in NIH3T3 and HEK293 cells. *J. Biol. Chem.* 274; 3414–3421.

Lewis B S, Flugelman M Y, Weisz A, Keren-Tal I, Schaper W. (1997) Angiogenesis by gene therapy; a new horizon for myocardial revascularization? Cardiovasc Res. 35:490–7.

Marinelli, R. A., Pham, L., Agre, P. & LaRusso, N. F (1997) Secretin promotes osmotic water transport in rat cholangiocytes by increased aquaporin-1 water channels in plasma membrane. *J. Biol. Chem.* 272; 12984–12988.

Minakata, Y., Suzuki, S., Grygorczyk, C., Dagenais, A & Berthiaume, Y. (1998) Impact of beta-adrenergic agonist on Na⁺ channel and Na⁺-K⁺-ATPase expression in avleolar type II cells. *Am. J. Physiol* 275; 414–422.

Morse M A.(2001) Technology evaluation: VEGF165 gene therapy, Valentis Inc. Curr Opin Mol Ther. 3; 97–101. Review.

Mutoh, H., Fung, B. P., Naya, F. J., Tsai, M. J., Nishitani, J. & Leiter, A. B (1997) The basic helix-loop-helix transcription factor BETA/NeuroD is expressed in mammalian enterendocrine cells and activates secretin gene expression. *Proc. Natl. Acad. Sci.* 94; 3560–3564.

Mutt, V., Jorpes, J. E. Magnusson, S. (1970) Structure of porcine secretin. The amino acid sequence. Eur. J. Biochem; 15; 513–519

Ng, S. S., Pong, R. T., Chow, B. K., Cheng, C. H. (1999) Real time evaluation of human secretin receptor activity using cytosensor microphysiometry. J. Cell. Biochem. 72; 517–527

Pendino, J. C., Nannin,i L. J., Chapman, K. R., Slutsky, A. & Molfino, N. A. (1998). Effect of inhaled furosemide in acute asthma. J. Asthma 35; 89–93

Robberecht, P., De Neef, P., Waelbroeck, M., Conius, J. C., Scemama, U. L., Fourmy, D., Pradayrol, L., Vaysse, N., Christophe, J. (1988) Secretin receptors in human pancreatic membrnaes. Pancreas 3; 529–535

Schmidt W E, Seebeck J, Höcker M, Schwarzhoff R, Schäfer H, Fornefeld H, Morys-Wortmann C, Fölsch UR, Creutzfeldt W. (1993) PACAP and VIP stimulate enzyme secretion in rat pancreatic acini via interaction with VIP/PACAP-2 receptors: additive augmentation of CCK/carbachol-induced enzyme release. *Pancreas* 8; 476-87

Sexton, P. M. (1999) Recent advances in our understanding of peptide hormone receptors and RAMPS. Curr. Opin. Drug Disc. Dev. 2; 440–448

Staun-Olsen, P., Ottesen, B., Gammeltoft, S. & Fahrenkrug, J. (1986) VIP binding sites on synaptosomes from rat cerebral cortex: structure-binding relationship. *Peptides* 7 *Suppl* 1; 181–186.

Suzuki S, Kawai K, Ohashi S, Mukai H, Yamashita K (1989) Comparison of the effects of various C-terminal and N-terminal fragment peptides of glucagon-like peptide-l on insulin and glucagon release from the isolated perfused rat pancreas. Endocrinology 125;3109–14

Turner, P. R., Bambino, T. & Nissenson, R. A. (1996) A putative selectivity filter in the G-protein-coupled receptors for parathyroid hormone and secretin. *J. Biol. Chem.* 271; 9205–9208

Waelbroeck, M., Robberecht, P., De Neef, P., Chatelain, P. & Christophe, J. (1981) Binding of vasoactive intestinal peptide and its stimulation of adenylate cyclase through two classes of receptors in rat liver membranes. Effect of 12 secretin analogues and 12 secretin fragments. *Biochim Biophys Acta* 678; 83–90.

Wearly, L. L (1991) Recent progress in protein and peptide delivery by non-invasive methods. Crit. Rev. Ther. Drug. Carrier System. 8; 333

West J, Rodman D M. (2001) Gene therapy for pulmonary diseases. Chest. 119; 613–7.

Xue, W., Chey, W. Y., Sun, Q., Chang, T. M. (1993) Characterisation of secretin release in secretin cell-enriched preparation isolated from canine duodenal mucosa. *Dig Dis Sci.* 38; 344–52

Yanaihara, N., Kubota, M., Sakagami, M., Sato, H., Mochizuki, T. (1977) Synthesis of phenolic group containing analogues of porcine secretin and their immunological properties. *J Med Chem* 20; 648–55

Yang Y, Quitschke W W, Brewer G J. (1998) Upregulation of amyloid precursor protein gene promoter in rat primary hippocampal neurons by phorbol ester, IL-1 and retinoic acid, but not by reactive oxygen species. *Brain Res Mol Brain Res.* 60; 40–9.

What is claimed is:

1. A method of treatment of cystic fibrosis in a patient suffering from cystic fibrosis, the method comprising administering to said patient an effective amount of human secretin comprising the sequence of SEQ ID NO:10.

2. The method of claim 1 wherein said human secretin is administered by inhalation.

3. The method of claim 1, wherein said human secretin is administered by a route selected from the group consisting of an intravenous, intramuscular and intraarticular route.

* * * * *

SEQUENCE LISTING

<160> NUMBER OF SEQ ID NOS: 13

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 1
gaccagcatc atctgagagg ct                                           22

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 2
ccttcgcagg acctctcttg                                              20

<210> SEQ ID NO 3

```
<211> LENGTH: 24
<212> TYPE: DNA
<213> ORGANISM: Artificial Sequence
<220> FEATURE:
<223> OTHER INFORMATION: Description of Artificial Sequence: Probe

<400> SEQUENCE: 3
tctctgtccg tgggtgaccc tgct                                           24

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 4
gaaggtgaag gtcggagtca ac                                             22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 5
cagagttaaa agcagccctg gt                                             22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Probe

<400> SEQUENCE: 6
tttggtcgta ttgggcgcct                                                20

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 7
gaacgcggcg ctagaca                                                   17

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 8
gtctcgattt tggacagctt ctg                                            23

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Probe

<400> SEQUENCE: 9
```

```
-continued agcaaggcac caccttgcgc a                                              21

<210> SEQ ID NO 10
<211> LENGTH: 27
<212> TYPE: PRT
<213> ORGANISM: Homo sapiens

<400> SEQUENCE: 10

His Ser Asp Gly Thr Phe Thr Ser Glu Leu Ser Arg Leu Arg Glu Gly
  1               5                  10                  15

Ala Arg Leu Gln Arg Leu Leu Gln Gly Leu Val
             20                  25

<210> SEQ ID NO 11
<211> LENGTH: 27
<212> TYPE: PRT
<213> ORGANISM: Sus sp.

<400> SEQUENCE: 11

His Ser Asp Gly Thr Phe Thr Ser Glu Leu Ser Arg Leu Arg Asp Ser
  1               5                  10                  15

Ala Arg Leu Gln Arg Leu Leu Gln Gly Leu Val
             20                  25

<210> SEQ ID NO 12
<211> LENGTH: 27
<212> TYPE: PRT
<213> ORGANISM: Canis sp.

<400> SEQUENCE: 12

His Ser Asp Gly Thr Phe Thr Ser Glu Leu Ser Arg Leu Arg Glu Ser
  1               5                  10                  15

Ala Arg Leu Gln Arg Leu Leu Gln Gly Leu Val
             20                  25

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      secretin analogue

<400> SEQUENCE: 13

Phe Phe Trp Lys
  1
```